US007887487B2

(12) United States Patent
Hao et al.

(10) Patent No.: US 7,887,487 B2
(45) Date of Patent: Feb. 15, 2011

(54) ULTRASOUND DIAGNOSTIC FLOW IMAGING WITH CODED EXCITATION

(75) Inventors: Xiaohui Hao, Redmond, WA (US); Kutay F. Ustuner, Mountain View, CA (US); Gregory L. Holley, Sunnyvale, CA (US); Seshadri Srinivasan, Mountain View, CA (US); Albert Gee, Los Altos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 830 days.

(21) Appl. No.: 11/303,622

(22) Filed: Dec. 15, 2005

(65) Prior Publication Data

US 2007/0038108 A1 Feb. 15, 2007

Related U.S. Application Data

(60) Provisional application No. 60/698,585, filed on Jul. 11, 2005.

(51) Int. Cl.
*A61B 8/00* (2006.01)
(52) U.S. Cl. ............... 600/455; 600/454; 600/457; 600/437; 600/463; 600/453; 73/631
(58) Field of Classification Search ............ 73/631
See application file for complete search history.

(56) References Cited

U.S. PATENT DOCUMENTS

| 4,509,526 | A | * | 4/1985 | Barnes et al. ............... 600/456 |
| 5,197,477 | A | * | 3/1993 | Peterson et al. ............ 600/454 |
| 5,211,179 | A | * | 5/1993 | Haberl et al. ............... 600/515 |
| 5,938,611 | A |  | 8/1999 | Muzilla et al. |
| 6,210,332 | B1 |  | 4/2001 | Chiao et al. |
| 6,213,947 | B1 | * | 4/2001 | Phillips .................. 600/443 |
| 6,309,356 | B1 | * | 10/2001 | Ustuner et al. ............. 600/443 |
| 6,375,618 | B1 | * | 4/2002 | Chiao et al. ................ 600/447 |
| 2004/0006266 | A1 | * | 1/2004 | Ustuner et al. ............. 600/407 |

OTHER PUBLICATIONS

"Zone-Based Color Flow Imaging," by Larry Y.L. Mo et al.; 2003 IEEE Ultrasonics Symposium; pp. 29-32.
"Coded Excitation for Diagnostic Ultrasound: A System Developer's Perspective," by Richard Y. Chiao and Xiaohui Hao; IEEE Transactions on Ultrasonics, Ferroelectrics, and Frequency Control, vol. 52, No. 2; Feb. 2005; pp. 160-170.
"Use of Modulated Excitation Signals in Medical Ultrasound. Part III: High Frame Rate Imaging," by Thanassis Misaridis and Jorgen Arendt Jensen; IEEE Transactions on Ultrasonics, Ferroelectrics, and Frequency Control, vol. 52 No. 2; Feb. 2005; pp. 208-219.
"Use of Modulated Excitation Signals in Medical Ultrasound. Part II: Design and Performance for Medical Imaging Applications," by Thanassis Misaridis and Jorgen Arendt Jensen; IEEE Transactions on Ultrasonics, Ferroelectrics, and Frequency Control, vol. 52, No. 2; Feb. 2005; pp. 192-207.
"Use of Modulated Excitation Signals in Medical Ultrasound. Part I: Basic Concepts and Expected Benefits," by Thanassis Misaridis and Jorgen Arendt Jensen; IEEE Transactions on Ultrasonics, Ferroelectrics, and Frequency Control, vol. 52, No. 2; pp. 177-191.

* cited by examiner

*Primary Examiner*—Long V Le
*Assistant Examiner*—Joel F Brutus

(57) ABSTRACT

Diagnostic ultrasound flow imaging is performed with coded excitation pulses. Due to the use of frequency coded excitation pulses, flow information may suffer from spatial misregistration and estimate errors. Spatial position shift in flow data is offset for alignment with B-mode or other imaging. The flow estimates are compensated for the imaging center frequency variation with depth. The wide bandwidth information available due to coded excitation may allow anti-aliasing by estimating velocities from two frequency bands.

27 Claims, 4 Drawing Sheets

ULTRASOUND DIAGNOSTIC FLOW IMAGING WITH CODED EXCITATION

RELATED APPLICATIONS

The present patent document claims the benefit of the filing date under 35 U.S.C. §119(e) of Provisional U.S. Patent Application Ser. No. 60/698,585, filed Jul. 11, 2005, which is hereby incorporated by reference.

BACKGROUND

The present embodiments relate to flow imaging. In particular, flow imaging is responsive to coded excitation pulses. Due to the trade-offs made to improve sensitivity, typical color flow imaging suffers from low resolution. However, diagnosis may benefit from high detail resolution information of blood flow hemodynamics, such as turbulence, volume jet, or flow profile.

For high-resolution flow imaging, uncoded wide bandwidth pulses may be used. However, a lack of sensitivity limits the usefulness of such pulses. Coded excitation pulses in B-mode imaging allow a trade-off between resolution and sensitivity. Coded pulses or pulses with nonlinear phase modulation in color Doppler imaging may improve sensitivity and possible detail resolution. However, coded excitation pulses in color flow imaging may result in inaccuracies.

BRIEF SUMMARY

By way of introduction, the preferred embodiments described below include methods, instructions and systems for ultrasound diagnostic flow imaging. Due to the use of coded excitation pulses, flow information may suffer from spatial misregistration and estimate errors. Spatial position shift in flow data is offset for alignment with B-mode or other imaging. The flow estimates are compensated for the imaging center frequency variation with depth. In addition to providing increased resolution, the wide bandwidth information available due to coded excitation may allow anti-aliasing by estimating velocities from two frequency bands. Any one or more of these features may be used.

In a first aspect, a method is provided for ultrasound diagnostic flow imaging. A plurality of coded excitation pulses is transmitted. A flow parameter is estimated as a function of the coded excitation pulses. A tissue image is generated separately with one of the coded excitation pulse or with tissue pulses. A spatial position of the flow parameter relative to the tissue image is offset if the tissue pulses are different from the coded excitation pulses.

In a second aspect, a method is provided for ultrasound diagnostic flow imaging. A plurality of coded excitation pulses is transmitted. A flow parameter is estimated as a function of the coded excitation pulses. The flow parameter or the estimation is corrected for a depth-dependent frequency shift.

In a third aspect, a method is provided for ultrasound diagnostic flow imaging. A plurality of coded excitation pulses is transmitted. A first flow parameter is estimated at a first frequency band as a function of the coded excitation pulses. A second flow parameter is estimated at a second frequency band as a function of the coded excitation pulses. The second frequency band is different from the first frequency band. Anti-aliasing is performed as a function of the first and second flow parameters.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Coded excitation pulses improve motion (e.g., fluid flow or tissue motion) imaging. A wide-band frequency-modulated or other coded pulse insonifies an object. The pulse is transmitted along the same position inside the object for at least two times, and a set of echo signals are received. A receive filter, such as a matched filter, decodes the received signals. A clutter filter removes information from stationary objects or objects associated with flow or tissue motion. An autocorrelator estimates the motion parameters such as power, velocity and variance. Using the coded excitation pulses, a large time-bandwidth product provides axial resolution and sensitivity improvements. A depth-dependent delay offset corrects for range mis-registration. A depth-dependent velocity estimator compensates for the center frequency downshift. The mis-registration and the frequency downshift are caused by frequency-dependent tissue attenuation. Two distinct bandwidth components of the wide-bandwidth receive signals allow anti-aliasing of the velocity estimates.

Figure 1:
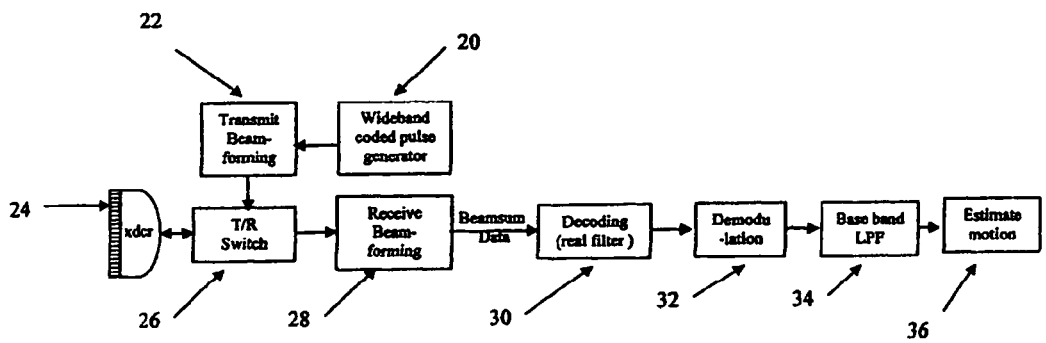
FIG. 1 is a block diagram of one embodiment of a system for ultrasound imaging with coded excitation pulses.

FIG. 1 shows a system and associated method for ultrasound diagnostic motion imaging with coded excitation pulses. Motion imaging includes imaging of fluid flow or tissue motion. The system includes a pulse generator 20, a transmit beamformer 22, a transducer 24, a transmit/receive switch 26, a receive beamformer 28, a decoding filter 30, a demodulator 32, a low pass filter 34, and motion estimator 36. Additional, different or fewer components may be used.

The pulse generator 20 is a waveform generator, pulser, digital-to-analog converter, memory, mixer, digital circuit, processor, switches, transistors, or other now known or later developed device for generating wideband coded pulses. The pulse generator 20 outputs a pulse coded by linear or non-linear frequency modulation, such as a chirp with a high time-bandwidth product, such as greater than 8 (e.g., 16). Other time-bandwidth products may be provided, such as greater than 1. For example, a 100% bandwidth up or down linear chirp at a 10 MHz center frequency with about 15-20 cycles and a Gaussian envelope is generated for each of a plurality of channels. Any other coded excitation may be used, such as a non-linear phase modulated coded excitation.

The transmit beamformer 22 includes delays, phase rotators, mixers, phase adjusters, amplifiers, combinations thereof or other now known or later developed beamformer components. The transmit beamformer 22 applies delay and apodization profiles across the transmit aperture. The profiles focus or direct the coded waveforms from the channels in the transmit aperture. Focused, broad, plane, weakly focused, divergent or other wavefronts may be formed.

The transmit/receive switch 26 is a diode switch or multiplexer. The switch 26 isolates the transmit beamformer 22 from the receive beamformer 28. The high voltage transmit waveforms are prevented from harming the low voltage receive circuits while allowing the use of the same transducer 24 for both transmit and receive operation. For transmit, the switch 26 routes the coded excitation pulses from the transmit beamformer 22 to the transducer 24.

The transducer 24 is a one-dimensional array of capacitive or piezoelectric elements. Multi-dimensional arrays may alternatively be used. The transducer 24 converts the electrical coded excitation waveforms to acoustic coded excitation pulses. The coded excitation pulses are transmitted, such as transmitting chirp excitations into a color flow region of interest. To estimate motion, multiple transmissions are performed with the same or different coded excitation pulses. The multiple transmissions are along a same scan line, but may be along a different scan line, at a different origin or at a different angle in other embodiments. Two or more, such as a sequence of 4-10 transmissions are performed for each scan line or region.

The transducer 24 receives acoustic echoes in response to the transmissions. Different elements receive different echo signals. The transducer 24 converts the echo signals into received electrical signals. A set of received signals are formed in response to each transmission of coded excitation pulses.

The transmit/receive switch 26 routes the received signals to the receive beamformer 28. The receive beamformer 28 includes filters, phase rotators, phase adjustors, delays, amplifiers, summers, combinations thereof or other now known or later developed receive beamformer components. The receive beamformer 28 applies relative delays and apodization across a receive aperture. The delayed and apodized received signals are summed to form receive data representing spatial locations.

The decoding filter 30 is a real or complex finite or infinite impulse response filter. The decoding filter 30 is a matched or partially matched filter to compress the long pulses responsive to the coded excitation pulses into shorter pulses, such as less than 3 cycles long. The shorter pulse length may increase resolution. For example, the resolution may be similar to B-mode resolution. Decoding filters 30 may be located in each channel for operating on data before beam summation to avoid receive focusing effect, or one decoding filter 30 may be located in the data path to operate on data after beam summation.

The demodulator 32 is a mixer, multiplier, clock, reference frequency source, combinations thereof or other now known or later developed demodulator. The demodulator 32 mixes the receive signals to base band. As shown, the demodulator 32 is positioned after the decoding filter 30. In other embodiments, the demodulator 32 is positioned prior to the decoding filter 30, such as being within the receive beamformer 28 to receive beam summed data. The low pass filter 34 removes high frequency components spaced from base band.

The motion estimator 36 is an autocorrelator, corner turning memory, clutter filter, processor, digital signal processor, application specific integrated circuit, field programmable gate array, Doppler processor, a software function block running on CPU, combinations thereof or other now known or later developed flow or motion processor. The motion estimator 36 estimates a flow or motion parameter as a function of the coded excitation pulses. For example, velocity, energy, variance or combinations thereof are estimated from decoded signals received in response to the chirp coded excitation pulses. The velocity, energy or variance is associated with fluid flow, tissue motion or combinations thereof. For example, a clutter filter removes high frequency (fluid flow) or low frequency (tissue motion) components from the receive signals prior to estimation of tissue motion or fluid flow, respectively.

Other components may be provided. For example, a B-mode detector connects with the receive beamformer 28. Using different receive signals responsive to no coding, different coding, or the same coding, an intensity or power representing tissue is detected. Alternatively, some of the same receive signals used by the estimator 36 are used to detect intensity or power. A tissue image is generated from the detected data. For example, a B-mode image is displayed or stored. The B-mode image displays intensities at different spatial locations in a Cartesian coordinate format. The different spatial locations correspond to scanned regions of a patient (e.g., regions in a polar or Cartesian format). A motion or flow image may be displayed in conjunction with the tissue image, such as overlaying a color, combining the two different signal sources or displaying the images adjacent to one another.

A spatial position of the motion parameter or data is offset relative to the tissue image or data in one embodiment. The offset better registers the motion image or data relative to the B-mode image or data. By offsetting along a range dimension, a range shift from a depth varying decoding filter responsive to depth dependent demodulation may be compensated, at least in part.

Figure 2:
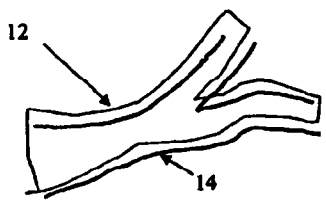
FIG. 2 is a graphical representation of an example flow region spatially mis-registered with a tissue image.

Frequency-dependent tissue attenuation shifts the center frequency of the received echo down with increased depth. Generally, to compensate for this center frequency shift for maxima signal-to-noise ratio, in receive, depth dependent demodulation frequency is employed for base band shifting. This depth dependent demodulation, together with the complex envelope for coding, produces a depth varying decoding filter which creates a depth dependent range shift of the received echo after decoding. The received signals register closer to the probe surface from the actual spatial location decided by the round trip time if an up-frequency sweep is used, or the received signals register away from the probe surface from the actual spatial location if a down-frequency sweep is used. Where the tissue image is associated with different transmit and/or receive characteristics, a mis-registration between motion and tissue representations exists. FIG. 2 shows a flow region 12 shifted closer to the transducer. The actual position for the flow region 12 is within the vessel walls 14.

A pulse coded by linear frequency modulation is represented as:

$$Tx(t) = e^{-\pi\left(\frac{t^2}{T_r^2} + j\frac{t^2}{T_i^2}\right)} e^{j2\pi f_m t} \supset Tx(f) = |T| e^{-\pi\left(\frac{1}{B_r^2} + j\frac{1}{B_i^2}\right)(f - f_m)^2} \quad (1)$$

and the receive pulse, ignoring any nonlinear effect is represented as:

$$Rx(f, r) = |T| e^{-\pi\left(\frac{1}{B_r^2} + j\frac{1}{B_i^2}\right)(f - f_m(r))^2} e^{-\alpha f r}, \quad (2)$$

where $f_m$ is the transmit modulation center frequency, $\alpha$ is the attenuation coefficient and $B_r$, $B_i$ are the real and imaginary bandwidth. The receive signals are demodulated to base band.

Assuming that $f_d(r)$ is the receive demodulation frequency as a function of depth r due to attenuation effect, and using the time reverse (and conjugate if complex) of the transmit signal envelope to form a decoding filter, the Fourier domain dictation of the decoding procedure can be shown as:

$$S(f, r) = |T|^2 e^{-\pi \frac{1}{B_r^2}[(f-f_m)^2+(f-f_d(r))^2]} e^{-\pi \frac{j}{B_i^2}[(f-f_d(r))^2-(f-f_m)^2]} e^{-\alpha f r} \quad (3)$$
$$= A e^{-\pi \frac{j}{B_i^2}(f_m-f_d)(2f-f_m-f_d(r))}$$

The group delay is represented by:

$$\Delta t(f, r) = \frac{1}{2\pi} \frac{\partial}{\partial f}\left[-\pi \frac{j}{B_i^2}(f_m - f_d(r))(2f - f_m - f_d(r))\right] \quad (4)$$
$$= -\frac{j}{B_i^2}(f_m - f_d(r)),$$

The range offset is calculated from above as:

$$\text{offset}(r) = 1540 * \Delta t / 2 = -0.77 * \frac{j}{B_i^2}(f_m - f_d(r)) \quad (5)$$

in units of mm where $f_m$, $f_d$, and $B_i$ are in MHz.

The mis-registration may be avoided by applying a constant demodulation frequency with $f_d(r) = f_m$. Signal-to-noise ratio (SNR) is sacrificed. Alternatively, the mis-registration is offset, allowing improved SNR.

In one embodiment shown in FIG. 1, receive signals responsive to the coded excitation pulses are decoded prior to demodulating the receive signals to offset or avoid the possible mis-registration between motion estimates and tissue image. The decoding occurs in the radio frequency domain (e.g., on RF or I/Q data). The decoding filter 30 is a long tap real decoding filter, such as a 64 or 128 tap finite impulse response filter. After decoding 30, range dependent demodulation increases the SNR. Other methods may be used to allow decoding of base band data with a filter having fewer taps.

Figure 3:
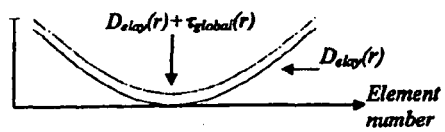
FIG. 3 is a graphical representation of one embodiment of additional delay for spatial compensation.

In another embodiment, an offset delay is applied in addition to focusing delays. A global receive delay at depth r ($\tau_{global}(r)$) for each range point along each beam compensates for the range shift. The delay offset at range r is calculated as:

$$\tau_{global}(r) = \text{offset}(r)/C_0. \quad (6)$$

where $c_0$ is the speed of sound. FIG. 3 shows an original focus delay profile and a focus delay profile with global delay offset for a certain time (or depth) across an array of elements. Each channel in the receive aperture applies the additional global delay during receive beamforming. The global delay is applied with the focusing delay as one delay value or the delays are performed in series. The global delay reverses the range dependent shift.

Figure 4A:
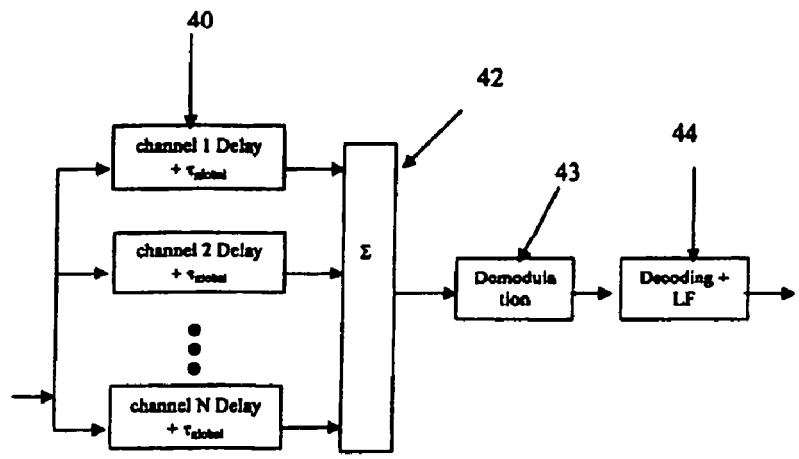
FIGS. 4A and B are flow chart diagrams of different beamforming related uses of the additional delay of FIG. 3 according to two embodiments, respectively.

FIG. 4A shows applying the global delay and channel focus delay as one value in act 40. The global compensation delay sums with the focus or steering delay data for each channel. In act 42, the delayed channel data is summed for later demodulation 43 and decoding 44.

Figure 4B:
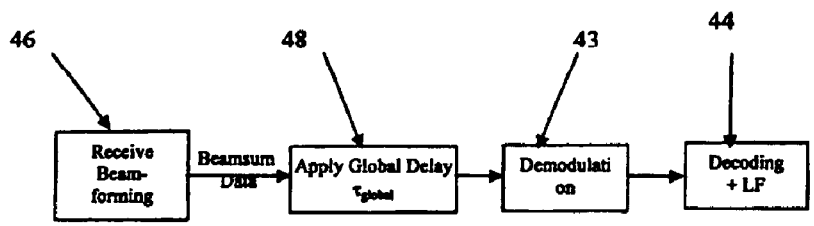

FIG. 4B shows applying the global delay to beam summed data. Receive signals are receive beamformed in act 46. The beamformed data is delayed by the global delay appropriate for each range in act 48. The offset data is then demodulated in act 43 and decoded in act 44.

Figure 5:
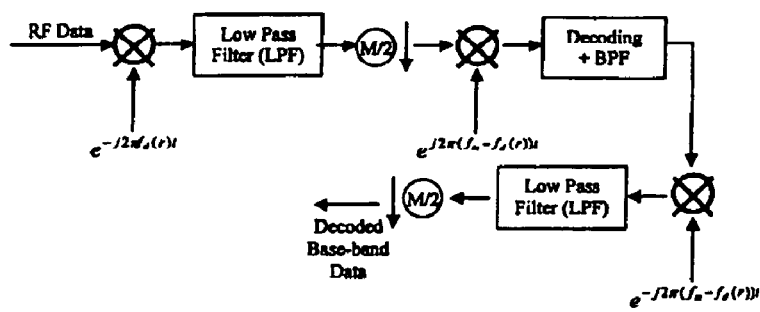
FIG. 5 is a flow chart diagram of one embodiment of demodulation and decoding operations for spatial compensation.

In another embodiment for offsetting, the demodulation is separated into multiple stages, such as three stages. The decoding occurs before the final demodulation. FIG. 5 shows one example embodiment. The received signals are demodulated with a depth dependent demodulation center frequency. The received signals demodulate to base band using a depth varying demodulation center frequency $f_d(r)$. $f_d(r)$ is an estimation based on the attenuation effect and may vary for different applications. A low pass base-band filter filters the base band data and decimates at a rate of M/2 or other value or function. M is a regular or desired total decimation rate for demodulation. The base band signals are modulated as a function of a difference between the depth dependent demodulation center frequency and a transmit modulation center frequency. The modulation shifts the signals away from base band in a range dependent function $\Delta f(r) = f_m - f_d(r)$. The modulated signals are decoded. The decoding filter is the time reverse and conjugation of the transmit signal demodulated by $f_m$ (e.g., IQ domain), represented as:

$$dec_{IQ}(t) = e^{-\pi\left(\frac{t^2}{T_r^2} - j\frac{t^2}{T_i^2}\right)}. \quad (7)$$

The decoding is followed with a band pass filter. The band pass is centered on the modulation shift and may change as a function of depth. The decoded signals are demodulated back to base-band. A demodulation frequency is set as the difference used for modulation, $\Delta f(r) = f_m - f_d(r)$. After base band filtering, the base band data is further decimated, such as with at a rate of M/2. The demodulation and decoding occur before or after beam summation. Part of the process, such as all the process before decoding, may occur before beam summation and the rest after beam summation.

In another method for offsetting, motion parameter locations are spatially remapped relative to the tissue image. For example, the remapping occurs during scan conversion, after scan conversion, or before scan conversion. Typically, during scan conversion, each range sample is assigned a spatial location in the display grid based on the receiving time. An algorithm changes the display spatial location for pixel k of the motion information. For example, the spatial location is modulated as:

$$Rn\_pos(k) = Rn\_cal(k) + \text{offset}(r_k). \quad (8)$$

In addition to or used separately from offset compensation, the motion parameter or the motion estimation is corrected for a depth-dependent frequency shift. Due to the strong depth dependence of the imaging center frequency in wide-bandwidth imaging, correction for the velocity estimate compensates for the imaging center frequency variation with depth.

The Doppler frequency shift $f_{Doppler}$ due to flow with a speed of $V_{flow}$ is given by:

$$f_{Doppler} = 2\frac{V_{flow}}{c} f_c(r)\cos(\theta) \quad (9)$$

where $f_c(r)$ is the depth dependent imaging center frequency, c is the speed of sound in the medium, and $\theta$ is the angle between the beam axis and the flow axis. The velocity estimate of the autocorrelation method is proportional to the mean Doppler frequency shift across the pulse bandwidth. Velocity or Doppler frequency shift is estimated as a function of a speed of sound and an imaging center frequency. In conventional color flow imaging, the flow velocity is estimated as:

$$\hat{v}_{flow} = \frac{c f_{Doppler}}{2 \hat{f}_c(r_0) \cos(\theta)} \quad (10)$$

where, $\hat{v}_{flow}$ is the estimation of the speed of flow or motion. $\hat{f}_c(r_0)$ is an estimated or predefined center frequency at a constant depth $r_0$. For narrow imaging bandwidths, selection of the predefined center frequency is convenient since $f_c(r) \approx f_c(0)$ due to narrow imaging bandwidths.

Figure 6:
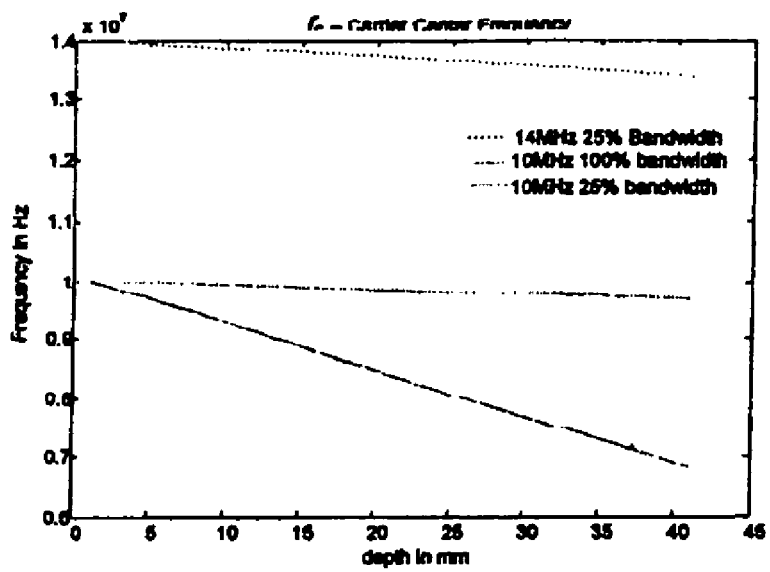
FIG. 6 is a graphical representation of example variation in frequency as a function of depth for different bandwidths.

For wider-bandwidth imaging, this approximation may not be appropriate. FIG. 6 shows an example of $f_c(r)$ for narrow-bandwidth and wide-bandwidth imaging. For the $f_c(0)=10$ MHz, 25% bandwidth pulse, the velocity error due to depth-independent imaging frequency assumption is negligible. However, for the $f_c(0)=10$ MHz, 100% bandwidth pulse, a depth-independent imaging center frequency of $\hat{f}_c(r_0=20$ mm) may result in a velocity estimate error of 17% at zero depth and 21% at 40 mm depth.

For wide bandwidth coded excitation pulses, the estimation is corrected by varying the imaging center frequency as a function of depth. A depth-dependent imaging center frequency may reduce velocity estimation errors. The velocity estimation is represented as:

$$\hat{v}_{flow} = \frac{c f_{Doppler}}{2 \hat{f}_c(r) \cos(\theta)} \quad (11)$$

where, $\hat{v}_{flow}$ is the estimation of the flow velocity. The $\hat{f}_c(r)$ can be either pre-determined using the imaging bandwidth and an assumed tissue attenuation coefficient, or estimated using the post-beamformer pre-detection data.

In another embodiment for correcting the estimation, velocity or frequency are estimated with the imaging center frequency substantially fixed as function of depth. The velocity or other motion parameters are altered as a function of depth. For example, a depth dependent look-up table or function alters the velocity estimates based on empirically determined corrections or the imaging bandwidth and a tissue attenuation coefficient. As another example, the estimate-to-color map accounts for the depth dependent estimation variation. The map may vary as a function of depth, such as provided a same color for different values at different depths or a different color for same values at different depths.

Figure 7:
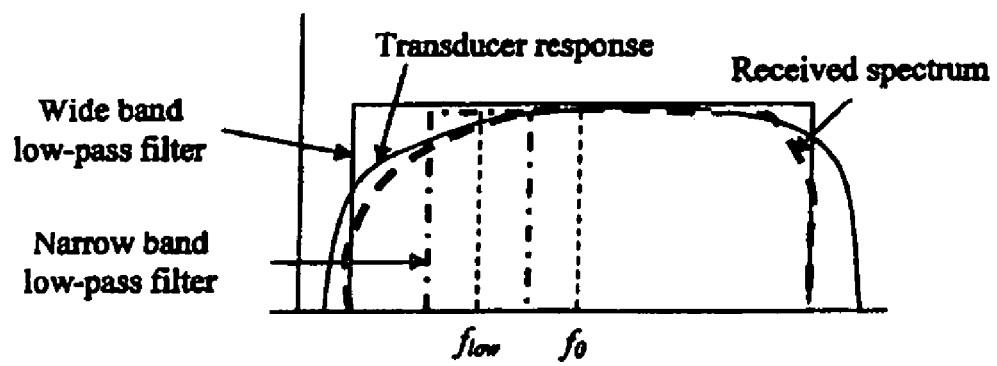
FIG. 7 is a flow chart diagram of one embodiment of anti-aliasing using coded excitation pulses.

In addition to or used separately from offset compensation and/or motion estimation correction, the received signals from coded excitation pulses are used for anti-aliasing velocity estimates. Velocity or other motion parameters are estimated in two different paths. FIG. 7 shows two different paths for demodulation 50, 52, base band filtering 54, 56, and color flow processing 58, 60 (i.e., estimating). Since the received signals responsive to coded excitation pulses have wide bandwidth, each path may estimate from signals at different frequency bands. The paths isolate the signals at the different frequency bands by demodulation and base band filtering. The received signals demodulate 50 to a low frequency ($f_{low}$) followed with low pass filtering 54 in one path. Color flow processes 58 estimate Doppler frequency shift estimates ($\Delta f_{low}$). The received signals also demodulate 52 to a center frequency ($f_0$), followed with low pass filtering 56. Color flow processes 60 estimate Doppler frequency shift estimates ($\Delta f_{wide}$).

Figure 8:
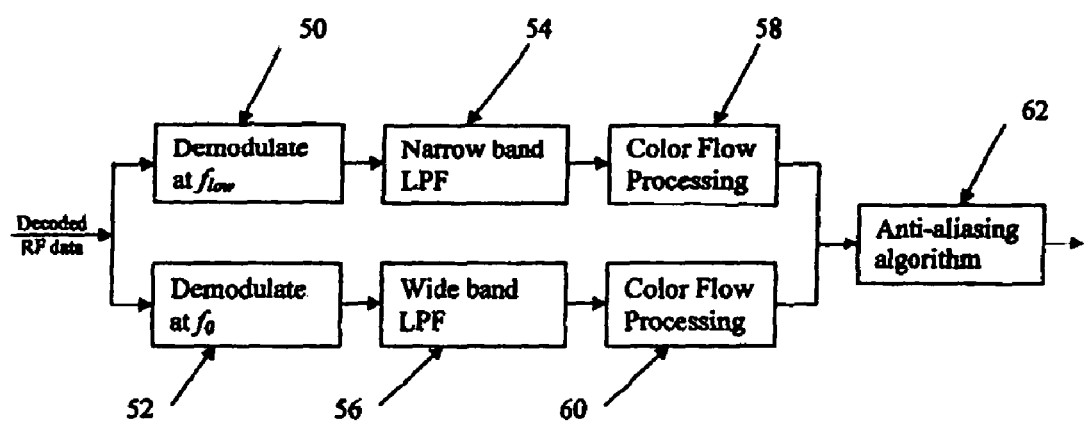
FIG. 8 is a graphical representation of demodulation and band pass filtering for anti-aliasing in one embodiment.

The different frequency bands have different center frequencies and/or bandwidths. For example, two relatively narrow frequency bands are used with different center frequencies, one higher and one lower. As another example, one path provides estimates for a narrow frequency band, and another path provides estimates for a wide frequency band at a same or different center frequency. FIG. 8 shows one example with a narrow frequency band (e.g., 25-50%) around a lower center frequency (e.g., 8 MHz) and a wide frequency band (e.g., 60-100%) around a higher center frequency (e.g., 10 MHz). The wide frequency band is 60% or more of a transducer response or a spectrum of the signals received in response to the coded excitation in one embodiment. The narrow frequency band is 40% or less of the transducer response or spectrum of the received signals in one embodiment.

Two paths or two passes in a same path for color flow processing, including demodulation, of the wide-bandwidth receive signals allow anti-aliasing of the velocity estimates with B-mode like resolution. The wideband and narrow band and/or low and high center frequency based velocity estimates are combined to produce a velocity estimate less likely to be aliased. Anti-aliasing is performed as a function of the flow parameters.

A third flow parameter, $\Delta f_3$, is predicted as a function of the first flow parameter and a ratio of the lower center frequency of the narrow frequency band to a higher center frequency of the wider frequency band. The wide band center frequency Doppler frequency shift estimate is predicted from the low frequency narrow band Doppler frequency shift estimates based on the frequency relationship ($\Delta f_3 = \Delta f_{low} * f_0 / f_{low}$). Other predictions using a different function or pass band relationship may be used. For example, the narrow band estimate is predicted. As another example, the ratio is of bandwidths, inversed and/or includes difference functions.

Aliased estimates are compensated by comparison of the predicted frequency shift to the estimated frequency shift. A difference from the predicted flow parameter to the estimated parameter is compared to a threshold. The threshold is a set or predefined value, but may be adaptive. For example, the threshold is the pulse repetition frequency of the coded excitation pulses divided by about two (e.g., 1.7-2.3). To account for positive and negative frequency shifts, the comparison is performed for negative and positive threshold values. In one embodiment, the comparison is represented by ($\Delta f_3 - \Delta f_{wide}$)>=PRF/2 or ($\Delta f_3 - \Delta f_{wide}$)=<-PRF/2.

If the difference is greater than the positive threshold or less than a negative threshold, the velocity is estimated from the narrow band frequency shift. For example, the velocity estimate is represented by:

$$\hat{v}_{flow} = \frac{c \Delta f_{low}}{2 \hat{f}_c(r) \cos(\theta)} \quad (12)$$

Otherwise, the velocity is estimated as a function of the wide band frequency shift and an inverse of the ratio used in the prediction. The estimate function is represented as:

$$\hat{v}_{flow} = \frac{c \Delta f_{wide}}{2 \hat{f}_c(r) \cos(\theta)} * \frac{f_{low}}{f_{wide}} \quad (13)$$

Other functions may be used.

In an alternative embodiment, velocities greater than a scale setting are truncated instead of scaled or compensated. Truncation is represented in one embodiment as: if $\Delta f_3 > PRF/2$, then $$\hat{V}_{flow} = \frac{cPRF}{4f_c(r)},$$

if $\Delta f_3 < -PRF/2$ then $$\hat{V}_{flow} = -\frac{cPRF}{4f_c(r)}.$$

Other functions may be used.

The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for ultrasound diagnostic motion imaging, the method comprising the acts of:
   transmitting a plurality of coded excitation pulses;
   estimating a motion parameter as a function of the coded excitation pulses, the motion parameter comprising velocity, energy, variance or combinations thereof, the motion parameter estimated for each of a plurality of locations;
   generating a tissue image;
   accounting for a misalignment caused by decoding the coded excitation pulses; and
   offsetting a spatial position, by the misalignment due to the use of the coded excitation pulses, of the motion parameters of the plurality of the locations relative to the tissue image.

2. The method of claim 1 wherein transmitting comprises transmitting chirp coded excitation pulses, estimating comprises estimating the velocity, energy, variance or combinations thereof from decoded signals received in response to the chirp coded excitation pulses, and generating the tissue image comprises generating a B-mode image; and further comprising:
   displaying a flow image with the B-mode image, the flow image being of the plurality of locations and being a function of the velocity, energy, variance or combination thereof;
   wherein offsetting comprises registering the flow image relative to the B-mode image.

3. The method of claim 1 wherein offsetting comprises offsetting along a range dimension.

4. The method of claim 1 wherein offsetting comprises compensating, at least in part, for a range shift from a depth varying decoding filter responsive to depth dependent demodulation.

5. The method of claim 1 wherein offsetting comprises applying an offset delay in addition to focusing delays.

6. The method of claim 1 wherein offsetting comprises:
   demodulating with a depth dependent demodulation center frequency;
   modulating signals as a function of a difference between the depth dependent demodulation center frequency and a transmit modulation center frequency;
   decoding the modulated signals; and
   demodulating the decoded signals back to base-band.

7. The method of claim 1 wherein offsetting comprises remapping spatially a motion parameter location relative to the tissue image.

8. The method of claim 1 further comprising:
   correcting the motion parameters or the estimation for a depth-dependent frequency shift.

9. The method of claim 1 wherein estimating comprises estimating the motion parameter at a first frequency band as a function of the coded excitation pulses;
   further comprising:
   estimating an additional flow parameter at a second frequency band as a function of the coded excitation pulses, the second frequency band different than the first frequency band; and
   anti-aliasing as a function of the flow parameters.

10. The method of claim 1 wherein accounting for a misalignment caused by decoding the coded excitation pulses comprises accounting for the misalignment caused by decoding the coded excitation pulses having a frequency sweep, the frequency sweep resulting in the misalignment.

11. A method for ultrasound diagnostic motion imaging, the method comprising the acts of:
   transmitting a plurality of coded excitation pulses into an object;
   estimating values of a motion parameter as a function of the coded excitation pulses for different locations, the motion parameter comprising velocity, energy, variance, or combinations thereof;
   correcting the values or the estimation of the values for a depth-dependent frequency shift due to frequency dependent tissue attenuation caused by use of the coded excitation pulses; and
   generating, using the values, an image as a function of the corrected motion parameter or estimation, the image comprising a velocity, energy, or variance image representing the different locations.

12. The method of claim 11 wherein correcting comprises compensating variation of an imaging center frequency with depth.

13. The method of claim 11 wherein estimating comprises estimating the velocity or Doppler frequency shift as a function of a speed of sound and an estimated receive imaging center frequency.

14. The method of claim 13 wherein correcting comprises correcting the estimation by varying the estimated receive imaging center frequency as a function of depth.

15. The method of claim 13 wherein estimating comprises estimating with the imaging center frequency substantially fixed as function of depth, and correcting comprises altering the velocity.

16. The method of claim 15 wherein altering the velocity comprises color mapping.

17. The method of claim 11 further comprising:
offsetting a spatial position of the motion parameter relative to a tissue image.

18. The method of claim 11 wherein estimating comprises estimating the flow parameter at a first frequency band as a function of the coded excitation pulses;
further comprising:
estimating an additional flow parameter at a second frequency band as a function of the coded excitation pulses, the second frequency band different than the first frequency band; and
anti-aliasing as a function of the flow parameters.

19. A method for ultrasound diagnostic flow imaging, the method comprising the acts of:
transmitting a plurality of coded excitation pulses into an object;
estimating a first flow parameter at a first frequency band as a function of the coded excitation pulses;
estimating a second flow parameter at a second frequency band as a function of the coded excitation pulses, the second frequency band different than the first frequency band;
anti-aliasing a velocity estimate as a function of the first and second flow parameters; and
generating an image as a function of the anti-aliased velocity estimate.

20. The method of claim 19 wherein:
estimating the first flow parameter comprises demodulating to a first center frequency of the first frequency band, filtering to the first frequency band and estimating flow; and
estimating the second flow parameter comprises demodulating to a second center frequency of the second frequency band, filtering to the second frequency band and estimating flow.

21. The method of claim 19 wherein estimating the first flow parameter comprises estimating the first flow parameter with data from the first frequency band, the first frequency band more narrow than the second frequency band.

22. The method of claim 21 wherein the second frequency band generally corresponds to 60% or more of a transducer response or a spectrum of signals received in response to the coded excitation pulses, the first frequency band generally corresponds to 40% or less of the transducer response or the spectrum, and the first frequency band has a first center frequency lower than a second center frequency of the second frequency band.

23. The method of claim 19 wherein anti-aliasing comprises:
predicting a third flow parameter as a function of the first flow parameter and a ratio of a second center frequency of the second frequency band to a first center frequency of the first frequency band, and
comparing a difference from the third flow parameter and the second flow parameter to a threshold.

24. The method of claim 23 wherein comparing comprises comparing to the threshold, the threshold being a pulse repetition frequency of the coded excitation pulses divided by about two.

25. The method of claim 23 wherein anti-aliasing further comprises estimating the velocity estimate as a function of the first flow parameter where the difference is greater than the threshold or less than a negative of the threshold or, otherwise, as a function of the second flow parameter and an inverse of the ratio.

26. The method of claim 23 wherein anti-aliasing further comprises truncating velocities greater than a scale setting.

27. The method of claim 19 further comprising:
offsetting a spatial position of the anti-aliased velocity estimate relative to a tissue image; and
correcting the anti-aliased velocity estimate or velocity estimation for a depth-dependent frequency shift.

* * * * *